United States Patent
Trout et al.

(10) Patent No.: US 6,504,003 B1
(45) Date of Patent: Jan. 7, 2003

(54) SYNTHESIS OF HIGHER POLYOL FATTY ACID POLYESTERS BY TRANSESTERIFICATION

(75) Inventors: James Earl Trout, West Chester, OH (US); Richard Gerard Schafermeyer, Cincinnati, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/646,295

(22) PCT Filed: Mar. 17, 1999

(86) PCT No.: PCT/US99/05619

§ 371 (c)(1),
(2), (4) Date: Sep. 15, 2000

(87) PCT Pub. No.: WO99/48946

PCT Pub. Date: Sep. 30, 1999

Related U.S. Application Data

(60) Provisional application No. 60/079,089, filed on Mar. 23, 1998.

(51) Int. Cl.$^7$ ................................................ C08G 63/02
(52) U.S. Cl. .................... 528/271; 426/601; 527/311; 528/176; 528/272
(58) Field of Search ................................ 528/176, 271, 528/272; 426/601; 527/311

(56) References Cited

U.S. PATENT DOCUMENTS

| | | |
|---|---|---|
| 3,480,616 A | 11/1969 | Osipow et al. |
| 3,600,186 A | 8/1971 | Mattson et al. |
| 3,714,144 A | 1/1973 | Feuge et al. |
| 3,963,699 A | 6/1976 | Rizzi et al. |
| 3,996,206 A | 12/1976 | Parker et al. |
| 4,298,730 A | 11/1981 | Galleymore et al. |
| 4,517,360 A | 5/1985 | Volpenhein |
| 4,861,613 A | 8/1989 | White et al. |
| 4,927,920 A | 5/1990 | Wagner et al. |
| 4,983,329 A | 1/1991 | Cooper |
| 4,983,731 A | 1/1991 | Wagner et al. |
| 5,175,323 A | 12/1992 | Cooper |
| 5,273,772 A | 12/1993 | Cooper |
| 5,288,884 A | 2/1994 | Cooper |
| 5,298,637 A | 3/1994 | Cooper |
| 5,304,665 A | 4/1994 | Cooper et al. |
| 5,362,894 A | 11/1994 | Handwerker et al. |
| 5,374,446 A | 12/1994 | Ferenz et al. |
| 5,387,429 A | 2/1995 | Cooper |
| 5,399,728 A | 3/1995 | Cooper |
| 5,399,729 A | 3/1995 | Cooper et al. |
| 5,427,815 A | 6/1995 | Ferenz |
| 5,466,843 A | 11/1995 | Cooper |
| 5,512,313 A | 4/1996 | Cooper et al. |
| 5,516,544 A | 5/1996 | Sekula et al. |
| 5,589,217 A | 12/1996 | Mazurek |
| 5,597,605 A | 1/1997 | Mazurek |
| 5,603,978 A | 2/1997 | White et al. |
| 5,641,534 A | 6/1997 | White et al. |

FOREIGN PATENT DOCUMENTS

| | | |
|---|---|---|
| DD | 262 663 A1 | 7/1988 |
| EP | 0 708 075 A1 | 4/1996 |
| EP | 0708075 * | 4/1996 |
| WO | WO 91/10368 | 7/1991 |
| WO | WO 97/22260 | 6/1997 |
| WO | WO 98/03526 | 1/1998 |
| WO | WO 99/48946 | 9/1999 |

OTHER PUBLICATIONS

Feuge, R.O., et al.—"Preparation of Sucrose Esters By Interesterification"; Journal of the American Oil Chemists' Society, vol. 47, Feb., 1970, pp. 56–60.

Perry, et al.—Chemical Engineers Handbook, 6$^{th}$ Edition, 1984, pp. 21–79.

Deuel, H.J. –The Lipids, 2, Interscience Publishers, Inc., New York, 1955, p. 215.

* cited by examiner

Primary Examiner—Terressa M. Boykin
(74) Attorney, Agent, or Firm—Karen F. Clark; Erich D. Hemm; Melody A. Jones

(57) ABSTRACT

A process for synthesizing polyol fatty acid polyesters comprising the steps of (1) mixing ingredients comprising (a) unesterified first polyol having hydroxyl groups, (b) second polyol esterified with fatty acids, (c) basic catalyst, and (d) emulsifying agent to form a mixture of ingredients; (2) reacting the mixture of ingredients at a temperature sufficient to obtain a transesterification reaction products and by-products; and (3) removing at least a portion of the by-products from the transesterification reaction mixture; and (4) further heating the transesterification reaction products and ingredients from step (3) at a temperature and for a time sufficient to esterify at least about 50% of the hydroxyl groups of the first polyol.

25 Claims, No Drawings

SYNTHESIS OF HIGHER POLYOL FATTY ACID POLYESTERS BY TRANSESTERIFICATION

This application claims the benefit of provisional application No. 60/079,089, filed Mar. 23, 1998.

This patent application cross-references and incorporates by reference co-pending patent application "Improved Processes for Synthesis and Purification of Nondigestible Fats", filed in the name of Trout et al, and co-pending application "Improved Processes for Synthesis and Purification of Nondigestible Fats Using Lipase", filed in the name of Trout et al., both applications filed on the same date as this application.

TECHNICAL FIELD

This invention relates to processes for the production of polyol fatty acid polyesters, which processes eliminate the need to synthesize and purify lower alkyl ester intermediates. More particularly, this invention relates to processes for synthesizing polyol fatty acid higher polyesters by reaction of unesterified polyol, preferably selected from the group consisting of monosaccharides, disaccharides, polysaccharides, sugar alcohols, sugar ethers, polyglycerols and polyalkoxylated glycerols, and a second polyol esterified with fatty acids and selected from monoglycerides, diglycerides and triglycerides.

BACKGROUND ART

The food industry has recently focused attention on polyol polyesters for use as low-calorie fats in food products. Triglycerides (triacylglycerols) constitute about 90% of the total fat consumed in the average diet. One method by which the caloric value of edible fat can be lowered is to decrease the amount of triglycerides that is consumed, since the usual edible triglyceride fats are almost completely absorbed in the human system (see *Lipids*, 2, H. J. Deuel, Interscience Publishers, Inc., New York, 1955, page 215). Low calorie fats which can replace triglycerides are described in Mattson, et al., U.S. Pat. No. 3,600,186. Mattson, et al. disclose low calorie, fat-containing food compositions in which at least a portion of the triglyceride content is replaced with a polyol fatty acid ester having at least four fatty acid ester groups, with each fatty acid having from eight to twenty-two carbon atoms.

Rizzi and Taylor, U.S. Pat. No. 3,963,699, describe a solvent-free transesterification process in which a mixture of a polyol (such as sucrose), a fatty acid lower alkyl ester (such as a fatty acid methyl ester), an alkali metal fatty acid soap, and a basic catalyst is heated to form a homogenous melt, to which is added excess fatty acid lower alkyl ester to form the higher polyol fatty acid polyesters. The polyesters are then separated from the reaction mixture. This process for making sucrose polyesters involves two discrete synthesis steps: (1) reaction of triglyceride and lower alkyl alcohol to form lower alkyl esters with glycerine (glycerol) as a by-product, and (2) reaction of sucrose and lower alkyl esters to form sucrose polyesters with a lower alkyl alcohol as a by-product.

Unfortunately, the need to synthesize fatty acid lower alkyl ester intermediates increases the operating costs of the polyol polyester synthetic process, and the reaction of polyol and fatty acid lower alkyl ester results in the production of lower alkyl alcohol as a by-product. Systems for the capture of lower alkyl alcohol are required, and the need to separate and handle the lower alkyl alcohol increases the risk of discharges of alcohol into the environment. Consequently, there exists a need to develop a transesterification process which does not employ fatty acid lower alkyl ester intermediates.

Feuge et al., U.S. Pat. No. 3,714,144, and Feuge et al., *J. Amer. Oil. Chem. Soc.*, 1970, 47(2), 56–60, disclose a solvent-free transesterification process which comprises mixing molten sucrose with esters of fatty acids and alkali-free sodium or potassium soaps under a partial vacuum. The teachings of Feuge et al. are primarily directed to the formation of lower esters; the only specific teaching by Feuge et al. of a method in which the percentage of sucrose esters having three or more fatty acid chains is greater than 35% of the total sucrose esters formed uses methyl carbitol palmitate as a fatty acid source. Unfortunately, methyl carbitol is relatively toxic and would be unsuitable for use in food grade polyol polyester production. The Feuge et al. article further teaches that triglycerides perform poorly as intermediates.

Osipow et al., U.S. Pat. No. 4,380,616, disclose the preparation of sucrose mono- and di-esters by forming a transparent emulsion containing immiscible reactants and maintaining the transparent emulsions under appropriate conditions to permit reaction. Sucrose mono- and di-esters are formed using emulsions containing methyl fatty acid ester and sucrose. Osipow et al. also disclose the formation of mono- and di-glycerides using emulsions containing glycerine and methyl fatty acid esters or glycerol tri-esters.

Parker et al., U.S. Pat. No. 3,996,206, teach that sucrose mono-and di-esters are valuable surfactants, while the sucrose octa-esters are unsatisfactory surfactants. Parker, et al., disclose a process for preparing lower sucrose polyester surfactants by reacting solid particulate sucrose with triglyceride in the presence of a basic transesterification catalyst; the triglyceride and sucrose are used in substantially equimolar amounts.

Gallymore et al., U.S. Pat. No. 4,298,730, disclose a process for preparing a surfactant mixture containing sucrose mono- and di-esters by reacting solid particulate sucrose with a fatty acid triglyceride, a di- and/or mono-glyceride, and a basic transesterification catalyst in the presence of a fatty acid soap. Gallymore et al. teach that sucrose octa-esters are unsatisfactory surfactants, and octa-esters are therefore not prepared in the process.

Cooper et al., U.S. Pat. No. 5,304,665, disclose a method of obtaining highly esterified alkoxylated polyols from triglycerides by contacting an epoxide, an aliphatic polyalcohol, and a triglyceride in the presence of a basic catalyst to accomplish ring-opening of the epoxide and formation of a partially esterified alkoxylated polyol, followed by contacting the partially esterified alkoxylated polyol with fatty acids.

Thus, many prior art methods which react triglycerides and polyol are limited to the synthesis of lower esters, and higher polyesters of polyhydroxy compounds, such as sucrose, are not or cannot be obtained. Additionally, many prior art two-step methods require a basic transesterification catalyst to be used in both steps. The use of such catalysts in both steps increases yield loss and increases color formation in the product. Other prior art methods require the addition of fatty acids in the second step.

SUMMARY OF INVENTION

Accordingly, it is an object of this invention to obviate various problems of the prior art.

It is another object of this invention to provide novel batch and continuous processes for the production of polyol polyesters, in particular polyol polyesters wherein at least 50%, preferably at least about 70%, more preferably at least about 75%, and even more preferably at least about 95%, of the polyol's hydroxyls are esterified. Preferred sucrose polyester products are sucrose higher polyesters in which an average of at least 4, and preferably an average of from about 5 to about 8, hydroxyls per polyol molecule are esterified.

It is also an object of this invention to provide novel processes for the production of polyol fatty acid polyesters, which processes eliminate the need to synthesize and purify fatty acid lower alkyl ester intermediates. The processes may be batch or continuous processes.

It is an additional object of this invention to provide novel processes for the production of polyol fatty acid polyesters which eliminate the need to ship, handle, capture, and/or recycle lower alkyl alcohol.

It is also an object of this invention to provide novel processes for the production of polyol fatty acid polyesters which eliminate discharge of lower alkyl alcohol to the environment.

It is yet another object of this invention to provide such processes which provide higher yields and which reduce undesirable color formation.

In accordance with one aspect of the present invention, there is provided both batch and continuous processes for synthesizing polyol fatty acid polyesters comprising the steps of (1) mixing ingredients comprising (a) unesterified first polyol having hydroxyl groups, (b) second polyol esterified with fatty acids, (c) basic catalyst, and (d) emulsifying agent selected from the group consisting of solvents, soaps, and partially esterified polyols, to form a mixture of ingredients; (2) reacting the mixture of ingredients at a temperature sufficient to obtain a reaction mixture of ingredients, reaction products and by-products; (3) removing at least a portion of the by-products from the reaction mixtures; and (4) further reacting the reaction products and ingredients from step (3) at a temperature and for a time sufficient to esterify at least 50%, preferably at least about 70%, more preferably at least about 75%, and most preferably at least about 95%, of the hydroxyl groups of the first polyol. The reaction can be continuous or batch. The basic catalyst, solvent and/or soap can be removed at the completion of the second step.

In accordance with another aspect of the present invention, there is provided processes for synthesizing polyol fatty acid polyesters comprising the steps of (1) mixing ingredients comprising (a) unesterified first polyol, preferably selected from a group consisting of monosaccharides, disaccharides, polysaccharides, sugar alcohols, sugar ethers, polyglycerols, and polyalkoxylated glycerols (b) second polyol esterified with fatty acid chains, (c) basic catalyst and (d) solvent to form a mixture of ingredients; (2) reacting the mixture of ingredients at a temperature sufficient to obtain a reaction mixture of ingredients, reaction products and by-products; and (3) removing at least a portion of the by-products from the reaction mixture; and (4) further reacting the reaction products and ingredients from step (3) at a temperature and for a time sufficient to esterify at least about 50%, preferably at least about 70%, more preferably at least about 75%, and most preferably at least about 95%, of the hydroxyl groups of the first polyol.

In accordance with another aspect of the present invention, there is provided processes for synthesizing sucrose higher polyesters (sucrose polyesters having more than four fatty acids) comprising the steps of (1) mixing ingredients comprising sucrose, fatty acid triglyceride, basic catalyst, and sucrose lower polyesters to form a mixture of ingredients; (2) reacting the mixture of ingredients at a temperature sufficient to obtain a reaction mixture of ingredients, reaction products and by-products; and (3) removing at least a portion of the by-products comprising glycerine, and mono- and di-glycerides from the reaction mixture; and (4) further reacting the reaction products and ingredients from step (3) at a temperature and for a time sufficient to complete the reaction, wherein the molar ratio of the fatty acids of the triglyceride to the hydroxyl groups of the sucrose is not less than 1:1. Preferably at least about 70%, by weight, of the sucrose higher polyesters are sucrose octa-esters.

It has now been found that higher sucrose polyesters can be produced without the use of lower alkyl ester intermediates or methyl carbitol by transesterification of sucrose by triglyceride. Glycerine, mono- and/or di-glycerides, the by-products of the reaction, are derived from the triglyceride when at least one ester group of the triglyceride has been transferred to sucrose. Removal of glycerine, mono- and/or di-glycerides drives the reaction to high degrees of esterification, and polyol penta- to octa-esters are formed. The need to produce fatty acid lower alkyl esters in a separate step and the need to separate lower alkyl alcohol are eliminated by these processes, resulting in more economic processes. Eliminating the production of lower alkyl alcohol also eliminates the risk of the alcohol being released into the environment It has also surprisingly been found that sucrose polyesters can be produced in a three-step process without using basic transesterification catalysts in the second step. Eliminating the basic transesterification catalyst from the second step provides higher yields and reduces undesirable color formation. A decrease in color formation increases the ease of product purification.

These and additional objects and advantages will be more fully apparent in view of the following detailed description.

DETAILED DESCRIPTION

The present invention encompasses continuous and batch transesterification processes for synthesizing polyol fatty acid polyester product, in particular highly esterified polyol fatty acid polyesters. Highly esterified polyol fatty acid polyesters are polyols wherein at least 50%, preferably at least about 70%, more preferably at least about 75%, and most preferably about 95%, of the hydroxyl groups are esterified. In one embodiment, the polyol fatty acid polyesters have at least 4, and more preferably an average of from about 5 to about 8, fatty acid groups per molecule. In another embodiment, the polyol fatty acid polyesters are esterified linked alkoxylated glycerins, esterified epoxide-extended polyols, and mixtures thereof.

A mixture of ingredients comprising an unesterified first polyol and an esterified second polyol is heated to obtain a transesterification reaction mixture of ingredients, reaction products and by-products. The transesterification reaction products comprise those compounds derived from the unesterified first polyol after one or more ester groups have been transferred from the esterified second polyol to the initially unesterified first polyol. The by-products of the transesterification reaction are those compounds derived from the initially esterified second polyol after one or more ester groups have been transferred from the second polyol to the initially unesterified first polyol. The removal of by-products from the transesterification reaction mixture drives the reaction of ingredients and reaction products to high degrees of transesterification. At least a portion of the by-products, preferably all the by-products, are removed during the polyol fatty acid polyester synthesis. Any remaining by-products can be removed during refinement of the resulting fatty acid polyesters.

Suitable polyol fatty acid polyester products include sucrose polyesters having on average at least four, preferably at least about five, ester linkages per molecule sucrose; the fatty acid chains preferably have from about eight to about twenty-four carbon atoms. Other suitable polyol fatty acid polyesters are esterified linked alkoxylated glycerins, including those comprising polyether glycol linking segments, as described in U.S. Pat. No. 5,374,446, incorporated herein by reference, and those comprising polycarboxylate linking segments, as described in U.S. Pat. Nos. 5,427,815 and 5,516,544, incorporated herein by reference; more preferred are those described in U. S. Pat. No. 5,516,544.

Additional suitable polyol fatty acid polyesters are esterified epoxide-extended polyols of the general formula $P(OH)_{A+C}$ $(EPO)_N$ $(FE)_B$ wherein P(OH) is a polyol, A is from 2 to about 8 primary hydroxyls, C is from about 0 to about 8 total secondary and tertiary hydroxyls, A+C is from about 3 to about 8, EPO is a $C_3-C_6$ epoxide, N is a minimum epoxylation index average number, FE is a fatty acid acyl moiety and b is an average number in the range of greater than 2 and no greater than A+C, as described in U.S. Pat. No. 4,861,613 and EP 0324010 A1. incorporated herein by reference. The minimum epoxylation index average number has a value generally equal to or greater than A and is a number sufficient so that greater than 95% of the primary hydroxyls of the polyol are converted to secondary or tertiary hydroxyls. Preferably the fatty acid acyl moiety has a $C_7-C_{23}$ alkyl chain.

Preferred esterified epoxide-extended polyols include esterified propoxylated glycerols prepared by reacting a propoxylated glycerol having from 2 to 100 oxypropylene units per glycerol with $C_{10}-C_{24}$ fatty acids or with $C_{10}-C_{24}$ fatty acid esters, as described in U.S. Pat. Nos. 4,983,329 and 5,175,323, respectively, both incorporated herein by reference. Also preferred are esterified propoxylated glycerols prepared by reacting an epoxide and a triglyceride with an aliphatic polyalcohol, as described in U.S. Pat. No. 5,304,665, incorporated herein by reference, or with an alkali metal or alkaline earth salt of an aliphatic alcohol, as described in U.S. Pat. No. 5,399,728, incorporated herein by reference. More preferred are acylated propylene oxide-extended glycerols having a propoxylation index of above about 2, preferably in the range of from about 2 to about 8, more preferably about 5 or above, wherein the acyl groups are $C_8-C_{24}$ preferably $C_{14}-C_{18}$, compounds, as described in U.S. Pat. Nos. 5,603,978 and 5,641,534, both incorporated herein by reference. Particularly preferred are fatty acid-esterified propoxylated glycerols which exhibit a sharp melting point before about 92 F (33 C.) and have a dilatomeric solid fat index at 92 F (33 C.) of less than about 30, as described in WO 97/2260, or which have a dilatomeric solid fat index of at least about 50 at 70 F (21 C.) and at least about 10 at 98.6 F (37 C.), as described in U.S. Pat. Nos. 5,589,217 and 5,597,605, both incorporated herein by reference.

Other suitable esterified epoxide-extended polyols include esterified alkoxylated polysaccharides. Preferred esterified alkoxylated polysaccharides are esterified alkoxylated polysaccharides containing anhydromonosaccharide units, more preferred are esterified propoxylated polysaccharides containing anhydromonosaccharide units, as described in U.S. Pat. No. 5,273,772, incorporated herein by reference As used herein, all ratios are molar ratios unless otherwise specified, and all percentages are by weight unless otherwise specified.

Step 1. Forming the Mixture of Ingredients

In the first step of the present process, ingredients comprising unesterified first polyol, second polyol esterified with fatty acids, basic catalyst and emulsifying agent are mixed to form a mixture of ingredients. The esterified second polyol and unesterified first polyol are mixed in a ratio which yields a molar ratio of the fatty acid chains of the esterified second polyol to the hydroxyl groups of the unesterified first polyol greater than 0.5:1, preferably greater than 1:1, more preferably greater than about 1.5:1, and most preferably greater than about 2.25:1.

As used herein, the term "unesterified first polyol" is intended to include any aliphatic or aromatic compound containing at least two free hydroxyl groups. In practicing the processes disclosed herein, the selection of a suitable unesterified polyol is simply a matter of choice. For example, suitable unesterified polyols can be selected from the following classes: saturated and unsaturated straight and branched chain linear aliphatics; saturated and unsaturated cyclic compounds, including heterocyclic compounds; or mononuclear or polynuclear aromatics, including heterocyclic aromatics. Carbohydrates and non-toxic glycols are preferred unesterified polyols. Monosaccharides suitable for use herein include, for example, mannose, galactose, glucose, arabinose, xylose, ribose, apiose, rhamnose, psicose, fructose, sorbose, tagatose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. Natural sugar alcohols which are suitable for use herein are sorbitol, mannitol, and galactitol. Particularly preferred classes of materials suitable for use herein include the monosaccharides, the disaccharides and sugar alcohols. Preferred unesterified polyols include glucose, fructose, glycerol, polyglycerols, sucrose, zylotol, alkoxylated sorbitols and alkoxylated sorbitans, alkoxylated polyglycerols, and sugar ethers; particularly preferred is sucrose.

Preferred unesterified alkoxylated polyols include alkoxylated glycerol, alkoxylated polyglycerols, alkoxylated sorbitols and alkoxylated sorbitans, alkoxylated polysaccharides, and linked alkoxylated polyols such as linked alkoxylated glycerins. Polyols may be alkoxylated with $C_3-C_6$ epoxides, such as propylene oxide, butylene oxide, isobutylene oxide, and pentene oxide, to produce epoxide-extended polyols having an epoxylation index minimum of at least about 2, preferably in the range of from about 2 to about 8, as described in U.S. Pat. No. 4,816,613, incorporated herein by reference. Polyols may be also alkoxylated with an epoxide, preferably a $C_3-C_{10}$ 1,2-alkylene oxide, in the presence of a ring-opening polymerization catalyst, as described in U.S. Pat. Nos. 5,399,729 and 5.512,313, incorporated herein by reference.

Suitable alkoxylated polyols are described in U.S. Pat. Nos. 4,983,329; 5,175,323; 5,288,884; 5,298,637; 5,362, 894; 5,387,429; 5,446,843; 5,589,217; 5,597,605; 5,603,978 and 5,641,534, all incorporated herein by reference. Suitable alkoxylated polyols include alkoxylated sugar alcohols, alkoxylated monosaccharides, alkoxylated disaccharides, alkoxylated polysaccharides, alkoxylated $C_2$–$C_{10}$ aliphatic diols, and alkoxylated $C_3$–$C_{12}$ aliphatic triols. Preferred alkoxylated $C_3$–$C_{12}$ aliphatic triols are alkoxylated glycerols, more preferred are propoxylated glycerols, and particularly preferred are propoxylated glycerols having from about 3 to about 21 moles of propylene oxide per mole glycerol. Preferred alkoxylated polysaccharides are alkoxylated polysaccharides containing anhydromonosaccharide units, more preferred are propoxylated polysaccharides containing anhydromonosaccharide units, as described in U.S. Pat. No. 5,273,772, incorporated herein by reference. Preferred linked alkoxylated glycerins include those comprising polyether glycol linking segments, as described in U.S. Pat. No. 5,374,446, incorporated herein by reference, and those comprising polycarboxylate linking segments, as described in U.S. Pat. Nos. 5,427,815 and 5,516,544, incorporated herein by reference; more preferred are those described in U.S. Pat. No. 5,516,544.

As used herein, the term "second polyol" is intended to include fatty acid esters of polyols, in which the hydroxyl groups are replaced with esters of fatty acids. The polyol component of the esterified second polyol can be the same polyol as the unesterified first polyol, but generally it will be different.

Suitable fatty acids used to esterify the second polyol can be derived from either saturated or unsaturated fatty acids. Suitable preferred fatty acids include, for example, capric, lauric, palmitic, stearic, behenic, isomyristic, isomargaric, myristic, caprylic, and anteisoarachadic. Suitable preferred unsaturated fatty acids include, for example, maleic, linoleic, licanic, oleic, eladic, linolenic, erythrogenic acids. Lower fatty acids having from 2 to 8 carbons can also be used herein. In a preferred embodiment of the invention the fatty acid chains of the esterified polyols have at least eight carbon atoms; in a more preferred embodiment the fatty acid chains have from about eight to about twenty-four carbon atoms.

Esterified polyols can be obtained from hydrogenated and unhydrogenated naturally occurring oils; soybean oil, palm kernel oil, palm oil, coconut oil, sunflower oil, safflower oil, corn oil, cottonseed oil, peanut oil, canola oil, high erucic acid rapeseed oil and hydrogenated high erucic acid rapeseed oil are preferred. Naturally occurring oils can contain free fatty acids along with esterified polyols, these fatty acids can be removed before using the esterified polyols. A preferred esterified polyol is a triglyceride; particularly preferred is a triglyceride in which the fatty acid chains have from about eight to about twenty-four carbon atoms. Triglyceride will result in the formation of glycerine and/or mono- and di-glycerides as by-products.

The second polyol is preferably compatible with food-grade polyols, suitable second polyols include, for example, triglycerides. The second polyol is preferably free of esters which have potentially toxic effects, such as, for example methyl carbitol.

Suitable basic catalysts include alkali metals such as sodium, lithium and potassium; alloys of two or more alkali metals such as sodium-lithium and sodium-potassium alloys; alkali metal hydrides, such as sodium, lithium and potassium hydride; alkali metal lower (C1–C4) alkyls such as butyl-lithium; and alkali metal alkoxides of lower (C1–C4) alcohols, such as lithium methoxide, potassium t-butoxide, potassium methoxide, and/or sodium methoxide. Potassium methoxide and sodium methoxide are preferred catalysts. Other suitable basic compounds include carbonates and bicarbonates of alkali metals and alkaline earth metals. A preferred class of basic catalysts include potassium carbonate, sodium carbonate, barium carbonate, or mixtures of these compounds having particle sizes that are less than about 100 microns, preferably less than about 50 microns. These preferred catalysts can be used in admixture with the more conventional basic catalysts, described above. The use of these catalysts is further disclosed in U.S. Pat. No. 4,517,360 (Volpenhein), the catalyst disclosure of which is incorporated herein by reference.

As used herein, the term "emulsifying agent" is intended to include substances capable of emulsifying and/or solubilizing the mixture of unesterified polyol and esterified polyol, such as soaps, partially esterified polyols, and solvents.

Suitable soaps include alkali metal fatty acids soaps. As used herein, the term "alkali metal fatty acid soaps" is intended to include the alkali metal salts of saturated or unsaturated fatty acids having from about eight to about twenty-four carbon atoms, preferably from about eight to about eighteen carbon atoms. Accordingly, suitable alkali metal fatty acid soaps include, for example, lithium, sodium, potassium, rubidium, and cesiun salts of the fatty acids described herein. Mixtures of fatty acids derived from soybean oil, sunflower oil, safflower oil, cottonseed oil and corn oil are preferred. Accordingly, preferred alkali metal fatty acid soaps include, for example, the potassium soap made from soybean oil fatty acids. Soap emulsifier is not essential after the first polyol has been partially esterified and there is sufficient partially esterified polyol to maintain the homogeneity of the reaction mixture. Removal of the soap can be accomplished by known techniques, e.g., by filtration, centrifugation, etc., since the soap is relatively insoluble in the reaction mixture at higher degrees of esterification.

As used herein, the term "partially esterified polyol" are those esters of the polyol wherein up to about 50% of the hydroxy groups of polyol have been esterified. Preferred emulsifiers include sucrose lower polyesters, i.e., sucrose polyesters having on an average less than about 4 fatty acid groups per molecule sucrose.

Suitable solvents include dimethylformamide (DMF), formamide, dimethyl sulfoxide or pyridine. The solvent can be removed from the reaction mixture of Step 1 through distillation prior to or subsequent to the removal of the reaction by-products. If the polyol polyester is to be an edible product, a solvent-free system is preferred; also preferred is a soap-free system. An especially preferred system is a solvent-free system of sucrose, sucrose lower polyesters, and triglyceride; when sucrose lower polyesters are used as the emulsifying agent there is no need to remove the emulsifying agent after the completion of the second step.

Step 2. Reacting the Mixture of Ingredients

In the second step of the present processes, the mixture of ingredients is reacted at a temperature sufficient to obtain a transesterification reaction mixture of ingredients, reaction products, and by-products. A sufficient temperature is a temperature that exceeds the activation energy of the transesterification reaction and which causes transesterification to occur. The activation energy will depend in part upon the amount and type of catalyst used, and on the type of first polyol and second polyol. Generally it is unnecessary to heat the mixture of ingredients to a temperature greater than 350° C. (662° F.).

Step 2 is performed at a temperature of up to about 350° C. (662° F.), preferably from about 15° C. (59° F.) to about 350° C. (662° F.), more preferably from about 50° C. (122° F.) to about 350° C. (662° F.), even more preferably from about 50° C. (122° F.) to about 200° C. (392° F.). Particularly preferred are temperatures of from 70° C. (158° F.) to 150° C. (302° C.). When sucrose is used as the unesterified first polyol, temperatures less than about 150° C. (302° F.) are preferred since sucrose tends to caramelize at higher temperature above about 150 C. (302 F.). The preferred temperature is dependent in part on the type of emulsifier used. Generally when solvents such as DMF are used as the emulsifier, the temperature can be from about 15° C. (59° F.) to about 200° C. (392° F.), preferably from about 50° C. (122° F.) to about 140° C. (284° F.). When partially esterified polyols or soap is used as the emulsifier the temperature can be from about 50° C. (122° F.) to about 350° C. (662°), preferably from about 50° C. (122° F.) to about 200° C. (392° F.), and more preferably from about 70° C. (158° F.) to about 150° C. (302° F.).

Step 2 is generally performed at a pressure of from about $1 \times 10^{-8}$ m Hg to about 3 m Hg. In one embodiment, a time range for Step 2 is from about 5 minutes to about 2 hours, preferably from about 10 minutes to about 60 minutes, although the reaction time can vary depending on remaining process conditions. Generally, the second step is completed when the transesterification reaction rate decreases, and generally less than about 50% of the first polyol hydroxyl groups are esterified.

After completion of Step 2, the basic catalyst is preferably removed. Catalyst removal can be accomplished by filtration and/or centrifugation.

Step 3. Removing By-Products

In Step 3, by-products, for example glycerine and/or mono- and di-glycerides when the esterified second polyol is triglyceride, are removed, thereby promoting further transesterification of the reaction products. The driving force of the reaction is provided by any process or means sufficient to remove these by-products in a way that allows the reaction to continue, such as distillation, liquid-liquid extraction, supercritical fluid extraction, and inert gas stripping.

Distillation can be performed at reduced pressure. A preferred embodiment utilizes short path distillation. A reduced pressure sufficient to remove by-products based on by-products' molecular weights and liquid phase concentrations is used. The pressure is preferably from about $10^{-5}$ mm Hg to about 100 mm Hg, more preferably from about $10^{-4}$ mm Hg to about 1 mm Hg, even more preferably from about $10^{-3}$ mm Hg to about $10^{-1}$ mm Hg, and most preferably from about $10^{-3}$ mm Hg to about $10^{-2}$ mm Hg.

Distillation can be performed at the boiling point of the by-products. The exact temperature which is used depends upon the molecular weight of the by-products which are to be removed and the pressure of the system. A preferred distillation temperature for Step 3 is from about 100° C. (212° F.) to about 350° C. (662° F.), more preferably about 140° C. (284° F.) to about 250° C. (482° F.). When sucrose is used as the unesterified first polyol the temperature of Step 2 is preferably less than about 150° C. (302° F.) in order to avoid caramelization of the unesterified sucrose. However, the partially esterified sucrose formed in Step 2 can be heated to higher temperatures in Step 3 (from about 100° C. to 350° C.) without caramelization. A nitrogen sparge can be used to promote agitation and by-product removal.

Step 4. Further Reacting the Mixture of Reaction Products and Ingredients

In step 4 the transesterification reaction products and ingredients are further reacted at a temperature for a time sufficient to esterify at least about 50%, preferably at least about 70%, and more preferably at least about 75%, of the hydroxyl groups of the first polyol. Most preferably, Step 4 proceeds for a time to complete the reaction, i.e., when at least about 95% of the first polyol's hydroxyls are esterified. When the first polyol is sucrose, the reaction is completed when about 70%, by weight, of the sucrose polyesters are octa-esters. One of ordinary skill in the art will appreciate that the exact time is dependent upon the temperature and pressure of the system.

Basic catalysts can be omitted, particularly when a sufficient reaction temperature in step 4 is provided. In one preferred embodiment, the mixture of reaction products and ingredients in Step 4 is substantially free of basic catalyst; as used herein "substantially free of basic catalyst" is intended to mean less than 0.05% by weight of the mixture. More preferably, the mixture of transesterification reaction products and ingredients contains less than 0.01% by weight catalyst, even more preferably the mixture of ingredients contains no catalyst.

The by-product removal of step 3 will generally occur simultaneously with step 4. It is also possible to sequentially remove by-products and further react the reaction products and ingredients. The process may alternate between step 3 and step 4 in a series of cycles.

The resulting polyol fatty acid polyester product can be centrifuged, water-washed, and bleached, for example, with silica gel, for refinement. Centrifugation can be performed with a disc stack centrifuge. Water-washing can be done in a stirred tank; the water level is from about 5% to about 18% by weight of unrefined polyester, the mixing time is from about 10 to about 30 minutes Preferred mixing vessels for water-washing are multistage columns with agitation. Multistage columns suitable for use with the present invention include, but are not limited to, rotary disc contractors, Oldshue-Rushton extractors, Scheibel extraction towers, Kuhni towers, and the like. These columns are discussed by Perry, et al. *Chemical Engineers Handbook*, 6th Edition, 1984, pages 21–77 to 21–79, incorporated herein by reference. The columns in Perry et al. are schematically shown with counter-current flow. A heavy liquid is fed from the top of a vertical column and removed from the bottom with a light liquid fed near the bottom and extracted near the top. The two streams of the present invention can be fed counter-current, i.e., the streams flow through the column in opposite directions, or co-current, i.e., both streams flow through the column in the same direction. When the two streams are fed at or near the same end of the column, they are normally removed at or near the opposite end of the column.

Baffles can be provided between stages within the column wherein the size and shape of the opening in the baffle is designed to provide the desired residence time within each stage and other process conditions. Likewise, within each stage, an impeller can be provided, and typically the impellers are connected to a single shaft which runs through the column. Thus, one shaft can drive all of the impellers, maintaining the agitation speed relatively constant within different stages. However, as can be appreciated, impellers with independent drive motors and/or gears can be provided at individual stages or between stages so that the respective impeller speeds vary from one stage to the next. Agitation speed within the column and within individual stages, the size and shape of the baffle openings separating stages and the number of stages are all design criteria which can be varied to achieve a desired purification.

Multistage columns can be provided with "calming" zones at one or both ends of the column. If a calming zone is provided, two phases can be separated through the use of two extraction ports, i.e., a first port for extracting the first phase and a second port for extracting the second phase.

In another embodiment, the water phase can be separated by centrifuging, such as with a disc stack centrifuge. Alternatively, the water phase can be separated by gravity settling.

The polyol polyester can then be dried to a moisture content of less than about 0.1% in a vacuum dryer. Silica gel bleaching can be performed by contacting dry silica with the polyol polyester in a stirred tank for 30 minutes; the silica level is preferably about 1% by weight of the polyol polyester. The silica gel can be separated from the polyol polyester with a filter press.

The following examples are intended to further clarify the invention and should not be construed as limitations. All ratios are molar ratios unless otherwise specified, percentages are by weight unless otherwise specified.

Supercritical Fluid Chromatography

The composition of the polyol polyester can be determined by supercritical fluid chromatography. A sample of polyglycerol ester is first silylated to derivatize any unreacted hydroxyl groups. The silylated sample is then injected into the supercritical fluid chromatograph (SFC). The esters are separated by degree of esterification on a DB1 capillary column and detected by a flame ionization detector. The distribution of esters is calculated by peak area from the chromatogram.

Equipment and Conditions
  SFC: Lee scientific series 6000 supercritical fluid chromatograph or equivalent;
  SFC Conditions:
    A) Capillary Column
       DB1, 0.2 u film, 50 u ID, 10 m. J&W Scientific
    B) Temperatures
       Oven–90 C.
       Detector–400 C.
    C) Pressure Program
       125–375 atmospheres at 10 atmospheres per minute with a
       final hold time of 10 minutes.
    D) $CO_2$
       SFC grade, Scott Specialty Gases
    E) Hydrogen
       Approximately 30 mL/minute
    F) Air
       Approximately 300–350 mL/minute
    G) Auxiliary Gas (Nitrogen)
       Approximately 25 mL/minute
    H) Syringe for SFC injection
       50 ul Hamilton
    I) Vials
       2 or 4 dram Kimble Glass Fischer Scientific #03-340-1C
    J) Hot Plate
       90 C.
    K) Filter
       0.45 u Alltech Associates #2092
    L) Disposable Syringe
       3.0 mL Fisher Scientific #14-823-39
Reagents
  BSTFA (bis(Trimethylsilyl)-trifluoroacetamide) Supelco, Inc. #3-3027; TMSI (Trimethylsilylimidazole) Supelco, Inc. #3-3068; Pyridine ACS Grade MCB #PX2020-01

Analyzing the Sample

The sample is melted completely and mixed well. A disposable pipet is used to weigh 80–100 mg of sample into a four dram vial. The sample weight is recorded. 1 mL of Pyridine and 1 mL of TMSI/BSTFA solution (mixed 5:1) is added to the vial. The vial is capped and heated on the hot plate at 90 C. for 15 minutes. The sample is allowed to cool. A 0.45-micron filter is placed on the end of a 3-cc disposable syringe. The derivatized standard is poured into the disposable syringe and filtered into a GC vial. The sample is injected into the Supercritical Fluid Chromatograph.

EXAMPLE 1

Step (1): Sucrose (50 g) and 412 g of commercially available C8-triglycerides are mixed in about a 6:1 molar ratio and solubilized in 750 ml dimethylformamide (DMF). Potassium carbonate (4 g) is added.

Step (2): The mixture is reacted for about 20 minutes at 120° C. (248° F.) at atmospheric pressure; the DMF is then removed by distillation. The reaction products are sucrose esters having an average of about 3.7 fatty acid groups per sucrose molecule. The reaction by-products are glycerol esters having an average of 2.3 fatty acid groups per glycerol molecule. At the end of Step (2) the mixture comprises:

| | |
|---|---|
| Monoglycerides | 5.5% |
| Diglycerides | 33.1% |
| Triglycerides | 36% |
| Sucrose | 0.1% |
| Sucrose monoester (SE1) | 0.6% |
| Sucrose diester (SE2) | 2.5% |
| Sucrose triester (SE3) | 6.2% |
| Sucrose tetraester (SE4) | 8.4% |
| Sucrose quintaester (SE5) | 4.2% |
| Sucrose hexaester (SE6) | 3.1% |
| Sucrose hepta ester (SE7) | 0.4% |
| Sucrose octa ester (SE8) | 0% |

Steps (3) and (4): Sodium methoxide (0.3 g) is added to 300 g of the material produced in Step (2). The mixture is reacted further for about 42 hours at about 140–160° C. (284–320° F.) and about 0.015 mm Hg pressure. Fluid is recirculated through a thin film evaporator. Glycerine and mono- and di-glycerides are simultaneously removed. The remaining reaction mixture comprises, by weight, about 76.4% sucrose esters, about 23% triglycerides, and about 0.67% diglycerides. The process results in the formation of highly esterified sucrose esters (about 78%, by weight, of the sucrose ester products were octa-esters).

EXAMPLE 2

Step (1): Sucrose (35 g) and 543 g of high oleic sunflower oil triglyceride are mixed in about a 6:1 molar ratio and solubilized in 525 ml of dimethylformamide (DMF). Potassium carbonate (3 g) is added.

Step (2): The mixture is reacted for about 65 minutes at 120° C. (248° F.) at atmospheric pressure; the DMF is then removed by distillation. At the end of Step (2) the mixture comprises about:

| | |
|---|---|
| Monoglycerides | 3.7% |
| Diglycerides | 31% |
| Triglycerides | 41% |
| Sucrose | 0.1% |

-continued

|     |      |
| --- | ---- |
| SE1 | 0.4% |
| SE2 | 2.4% |
| SE3 | 5.1% |
| SE4 | 7.2% |
| SE5 | 6.3% |
| SE6 | 2.9% |
| SE7 | 0.4% |

Steps (3) and (4): Sodium methoxide (0.3 g) is added to 300 g of the material produced in Step (2). The mixture is reacted further for about 76 hours at 150–230° C. (302–446° F.), and $60 \times 10^{-3}$ mm Hg to $20 \times 10^{-3}$ mm Hg. Fluid is recirculated through a thin film evaporator. Glycerine and mono- and di-glycerides are simultaneously removed. The process results in the formation of highly esterified sucrose esters (about 70% of the sucrose polyesters were octa-esters).

The remaining reaction mixture comprises about:

|              |       |
| ------------ | ----- |
| Diglycerides | 1.8%  |
| Triglycerides| 62%   |
| SE6          | 2.2%  |
| SE7          | 8.6%  |
| SE8          | 25.3% |

The mixture comprises no monoglycerides or lower sucrose esters.

EXAMPLE 3

Steps (1) and (2): Sucrose ester feed material is produced by transesterification of soybean methyl esters with sucrose. The crude material is washed, dried under vacuum, bleached with silica gel, and filtered. The excess methyl esters are removed on a wiped film evaporator. The sucrose ester feed material composition is about:

|     |       |
| --- | ----- |
| SE1 | 0.2%  |
| SE2 | 0.4%  |
| SE3 | 2.4%  |
| SE4 | 6.8%  |
| SE5 | 14.5% |
| SE6 | 23.8% |
| SE7 | 28.8% |
| SE8 | 20.9% |

Steps (3) and (4): The sucrose ester feed material (6580 g) and 4770 g of triglycerides from a corn/canola oil blend are mixed. Catalyst, 55 g of 25% sodium methoxide in methanol, is added.

The mixture is reacted at a temperature of about 225° C. (437° F.) and a pressure of about $2 \times 10^{-3}$ mm Hg to about $4 \times 10^{-3}$ mm Hg. The mix is passed 41 times through a molecular still. The total residence time of the passes is about 6 minutes.

Short path distillation is utilized to remove the transesterification reaction by-products. A wiped film evaporator with an internal condenser is used.

The process results in the formation of highly esterified sucrose esters (about 75% of the sucrose polyesters were octa-esters.) The remaining reaction mixture comprises about:

|               |        |
| ------------- | ------ |
| Diglycerides  | 0.81%  |
| Triglycerides | 82.8%  |
| SE6           | 0.81%  |
| SE7           | 2.95%  |
| SE8           | 11.48% |

The mixture comprises no monoglycerides or lower sucrose esters.

The proceeding examples are set forth to illustrate specific embodiments of the invention, and are not intended to limit the scope of the methods of the present invention. Additional embodiments and modifications within the scope of the claimed invention will be apparent to one of the ordinary skill in the art. Accordingly, the scope of the present invention shall be considered in the terms of the following claims, and is understood not to be bound by or limited to the details of the methods described in the specification.

What is claimed is:

1. A process for synthesizing polyol fatty acid polyesters comprising the steps of:
   (1) mixing ingredients comprising (a) unesterified first polyol having hydroxyl groups, (b) second polyol esterified with fatty acids, (c) basic catalyst, and (d) emulsifying agent to form a mixture of ingredients;
   (2) reacting the mixture of ingredients at a temperature sufficient to obtain a transesterification reaction mixture comprising ingredients, transesterification reaction products and by-products, wherein the mixture of ingredients is reacted at a temperature of from about 15 C. to about 350 C.;
   (3) removing at least a portion of the by-products from the transesterification reaction mixture; and
   (4) further reacting the transesterification reaction products and ingredients from step (3) at a temperature and for a time sufficient to esterify at least about 50% of the hydroxyl groups of the first polyol;
   wherein the unesterified first polyol is selected from the group consisting of monosaccharides, disaccharides, oligosaccharides, polysaccharides, sugar alcohols, sugar ethers, polyglycerols and polyalkoxylated glycerols; and
   wherein the second polyol is derived from hydrogenated and unhydrogenated naturally occurring oils selected from the group consisting of soybean oil, cottonseed oil, palm kernel oil, palm oil, coconut oil, sunflower oil, safflower oil, corn oil, cottonseed oil, peanut oil, canola oil, high erucic acid rapeseed oil, hydrogenated high erucic acid rapeseed oil and mixtures thereof; and
   wherein the basic catalyst is selected from the group consisting of alkali metals, alloys of alkali metals, alkali metal hydrides, alkali metal alkoxides, alkali metal carbonates, alkali metal bicarbonates, and mixtures thereof.

2. A process according to claim 1, wherein step (3) and step (4) occur simultaneously.

3. A process according to claim 1, wherein step (3) and step (4) occur in at least one cycle of step (3) followed by step (4).

4. A process according to claim 1, wherein the unesterified first polyol is selected from the group consisting of monosaccharides, disaccharides, oligosaccharides, polysaccharides, sugar alcohols, sugar ethers, polyglycerols and polyalkoxylated glycerols.

5. A process according to claim 1, comprising the step of removing the basic catalyst after the completion of step (2).

6. A process according to claim 5, comprising the step of heating a mixture of reaction products and ingredients in step (3) wherein the mixture is substantially free of basic catalyst.

7. A process according to claim 1, comprising the step of removing the emulsifying agent after the completion of step (2).

8. A process according to claim 1, wherein the mixture of ingredients is reacted in step (2) at a temperature of from about 15 C to about 350 C.

9. A process according to claim 1, wherein the unesterified first polyol is sucrose and the emulsifying agent is sucrose lower polyesters.

10. A process according to claim 1, wherein the second polyol is derived from hydrogenated and unhydrogenated naturally occurring oils selected from the group consisting of soybean oil, cottonseed oil, palm kernel oil, palm oil, coconut oil, sunflower oil, safflower oil, corn oil, cottonseed oil, peanut oil, canola oil, high erucic acid rapeseed oil, hydrogenated high erucic acid rapeseed oil and mixtures thereof.

11. A process according to claim 1, wherein the second polyol is a triglyceride.

12. A process according to claim 1, wherein the basic catalyst is selected from the group consisting of alkali metals, alloys of alkali metals, alkali metal hydrides, alkali metal alkoxides, alkali metal carbonates, alkali metal bicarbonates, and mixtures thereof.

13. A process according to claim 1, wherein the mixture of ingredients has a molar ratio of fatty acids of the second polyol to hydroxyl groups of the unesterified first polyol of greater than about 1:1.

14. A process according to claim 1, wherein the reacting of step (4) is for a time sufficient to esterify at least about 70% of the first polyol hydroxyl groups of the first polyol.

15. A process according to claim 1, wherein the reacting of step (4) is for a time sufficient to esterify at least about 95% of the first polyol hydroxyl groups of the first polyol.

16. A process according to claim 1, comprising the step of removing the by-products from the reaction mixture in step (3) by distilling at reduced pressure.

17. A process according to claim 16, comprising distilling at a pressure of from about $10^{-5}$ mm Hg to about 100 mm Hg.

18. A process according to claim 1, comprising the step of removing the by-products from the reaction mixture in step (3) by distilling at a temperature of from about 100° C. to about 350° C. at a pressure of about $10^{-4}$ mm Hg to about 1 mm Hg.

19. A process according to claim 1, wherein the process is a batch process.

20. A process according to claim 1, wherein the process is a continuous process.

21. A process according to claim 1, wherein the polyol fatty acid polyesters comprise a polyol fatty acid polyesters selected form the group consisting of esterified linked alkoxylated glycerins, esterified epoxide-extended polyols, and mixtures thereof.

22. A process for synthesizing polyol fatty acid polyesters comprising the steps of:

(1) mixing ingredients comprising (a) unesterified first polyol having hydroxyl groups and being selected from a group consisting of monosaccharides, disaccharides, oligosaccharides, polysaccharides, sugar alcohols, sugar ethers, polyglycerols and polyalkoxylated glycerols, (b) second polyol esterified with fatty acids, (c) basic catalyst and (d) solvent to form a mixture of ingredients;

(2) reacting the mixture of ingredients at a temperature sufficient to obtain a transesterification reaction mixture comprising ingredients, transesterification reaction products and by-products;

(3) removing the solvent through distillation; and (4) removing the by-products from the transesterification reaction mixture; and (5) further reacting the transesterification reaction products and ingredients from step (3) at a temperature and for a time sufficient to esterify at least about 50% of the hydroxyl groups of the first polyol.

23. A process according to claim 22, wherein the solvent is selected from the group consisting of dimethylformamide, formamide, dimethyl sulfoxide, and pyridine.

24. A process for synthesizing sucrose higher polyesters comprising the steps of:

(1) mixing ingredients comprising sucrose, fatty acid triglyceride, basic catalyst and sucrose lower polyesters to form a mixture of ingredients;

(2) reacting the mixture of ingredients at a temperature sufficient to obtain a transesterification reaction mixture; said reaction mixture comprising ingredients, reaction products and by-products comprising glycerine and mono- and di-glycerides;

(3) removing the by-products comprising glycerine, and mono- and di-glycerides from the transesterification reaction mixture, and (4) further reacting the reaction products and ingredients from step (3) at a temperature and for a time sufficient to complete the reaction;

wherein the molar ratio of fatty acids of the triglyceride to hydroxyl groups of the sucrose is not less than 1:1.

25. A process according to claim 23, wherein at least about 70%, by weight, of the sucrose higher polyester are sucrose octa-esters.

* * * * *